(12) United States Patent
Maschke et al.

(10) Patent No.: US 8,548,567 B2
(45) Date of Patent: Oct. 1, 2013

(54) SYSTEM FOR PERFORMING AND MONITORING MINIMALLY INVASIVE INTERVENTIONS

(75) Inventors: Michael Maschke, Lonnerstadt (DE); Reinmar Killmann, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 1883 days.

(21) Appl. No.: 11/486,356

(22) Filed: Jul. 13, 2006

(65) Prior Publication Data
US 2007/0027390 A1 Feb. 1, 2007

(30) Foreign Application Priority Data

Jul. 13, 2005 (DE) .......................... 10 2005 032 755

(51) Int. Cl.
*A61B 5/05* (2006.01)
*A61B 8/12* (2006.01)
*A61N 1/00* (2006.01)

(52) U.S. Cl.
USPC ........... 600/427; 600/410; 600/411; 600/437; 600/439; 600/462; 600/467; 378/4

(58) Field of Classification Search
None
See application file for complete search history.

(56) References Cited

U.S. PATENT DOCUMENTS

| 5,409,000 A | 4/1995 | Imran |
| 5,646,525 A | 7/1997 | Gilboa |
| 5,706,416 A | 1/1998 | Mann et al. |
| 6,038,468 A | 3/2000 | Rex |

(Continued)

FOREIGN PATENT DOCUMENTS

| DE | 100 47 364 A1 | 4/2002 |
| DE | 102 10 645 A1 | 10/2003 |

(Continued)

OTHER PUBLICATIONS

"MRI Shielding for Medical Devices"; Biophan Technologies, Inc.; [retrieved from Internet on Jul. 11, 2005]; pp. 1-5.

(Continued)

*Primary Examiner* — Long V. Le
*Assistant Examiner* — Bradley Impink

(57) ABSTRACT

The present invention relates to a system for performing and monitoring minimally invasive interventions with an x-ray unit, in which at least one x-ray source and one x-ray detector can traverse a circular track through an angle range, an ECG recording unit, an imaging catheter, a mapping unit with a mapping catheter and an ablation unit with an ablation catheter. The system comprises a control and evaluation unit with interfaces for the units and catheters, which enable an exchange of data with the control and evaluation unit. The control and evaluation unit is designed for processing measurement or image data which it receives from the catheters and units, and for controlling the catheters and units for the capture of the measurement or image data. The workflow from the examination through to the therapy, particularly with regard to the treatment of tachycardial arrhythmias, is covered completely and continuously by the proposed system.

18 Claims, 1 Drawing Sheet

(56) References Cited

U.S. PATENT DOCUMENTS

| | | | |
|---|---|---|---|
| 6,148,823 | A | 11/2000 | Hastings |
| 6,379,041 | B1 | 4/2002 | Schuetz et al. |
| 6,506,972 | B1 | 1/2003 | Wang |
| 6,556,695 | B1 | 4/2003 | Packer et al. |
| 6,738,673 | B2 | 5/2004 | Desai |
| 6,772,001 | B2 | 8/2004 | Maschke |
| 2002/0049375 | A1* | 4/2002 | Strommer et al. ............ 600/407 |
| 2002/0181645 | A1 | 12/2002 | Bruder et al. |
| 2003/0040674 | A1 | 2/2003 | Corl et al. |
| 2003/0050557 | A1* | 3/2003 | Susil et al. ................... 600/424 |
| 2003/0181809 | A1* | 9/2003 | Hall et al. ..................... 600/425 |
| 2003/0199748 | A1 | 10/2003 | Camus et al. |
| 2003/0220561 | A1 | 11/2003 | Camus et al. |
| 2004/0008882 | A1 | 1/2004 | Hornegger et al. |
| 2004/0009459 | A1* | 1/2004 | Anderson et al. ............ 434/262 |
| 2004/0066906 | A1 | 4/2004 | Hornegger et al. |
| 2004/0097806 | A1* | 5/2004 | Hunter et al. ................. 600/434 |
| 2004/0193042 | A1* | 9/2004 | Scampini et al. ............. 600/424 |
| 2005/0058248 | A1 | 3/2005 | Klingenbeck-Regn |
| 2005/0107688 | A1* | 5/2005 | Strommer ..................... 600/424 |
| 2005/0148836 | A1 | 7/2005 | Kleen et al. |

FOREIGN PATENT DOCUMENTS

| | | |
|---|---|---|
| DE | 102 10 646 A1 | 10/2003 |
| DE | 103 06 068 A1 | 6/2004 |
| DE | 102 55 957 A1 | 8/2004 |
| DE | 103 55 275 A1 | 7/2005 |
| EP | 0 885 594 B1 | 12/1998 |
| EP | 1 182 619 A2 | 2/2002 |
| WO | WO 00/43730 A1 | 7/2000 |
| WO | WO 01/11409 A2 | 2/2001 |

OTHER PUBLICATIONS

Ulrich Walter, Eckart Hundt; "Autostereoskopische 3D-Displays und—Verfahren"; Technology. Report CT IRC TIS, Oct. 2003; pp. 1-276.

E. Euler, S. Heining, T. Fischer, K.J. Pfeifer, W. Mutschler; "Initial Clinical Experiences with the SIREMOBIL Iso-C$^{3D}$"; Electromedica 70; 2002; pp. 48-51; No. 1.

* cited by examiner

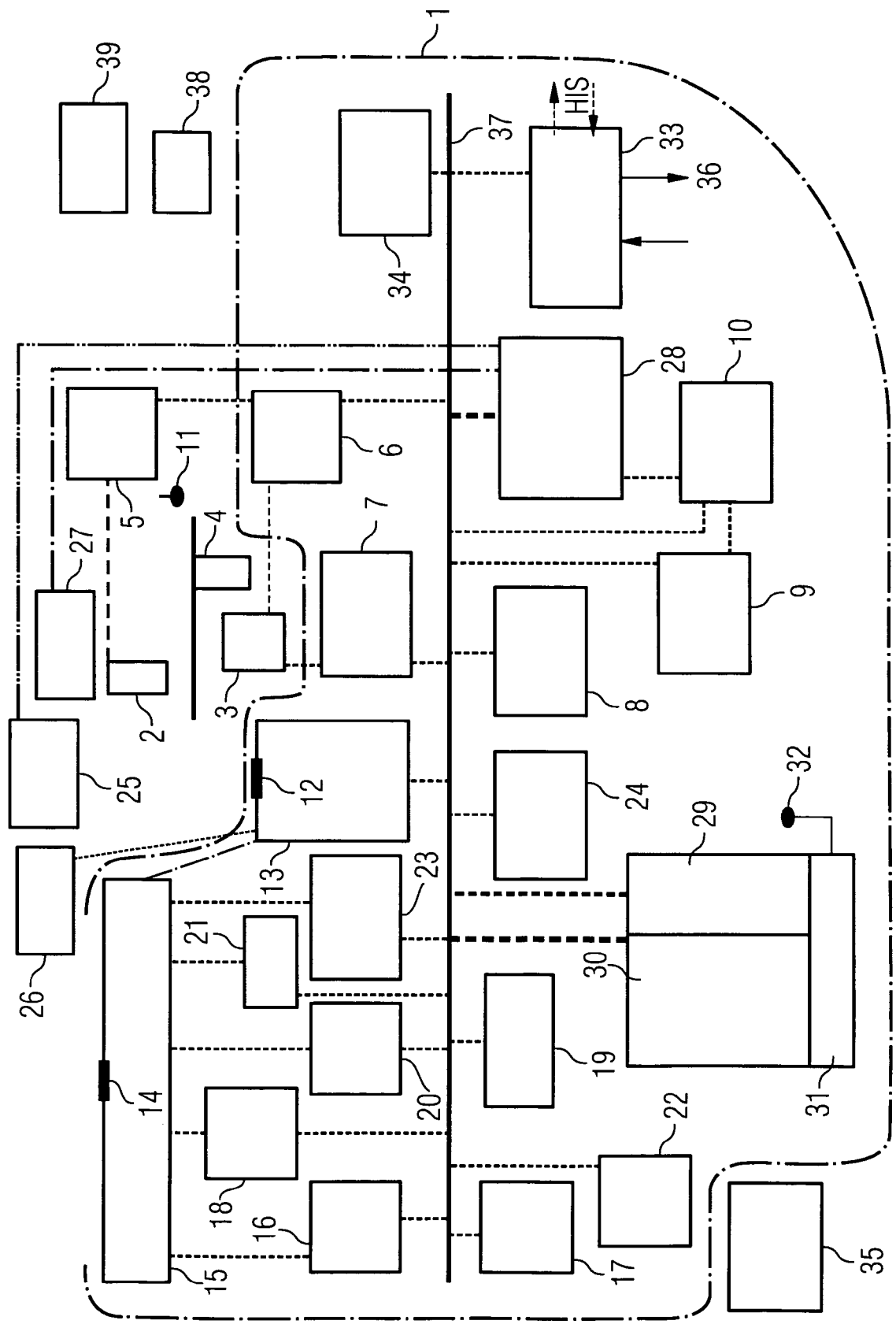

SYSTEM FOR PERFORMING AND MONITORING MINIMALLY INVASIVE INTERVENTIONS

CROSS REFERENCE TO RELATED APPLICATIONS

This application claims priority of German application No. 10 2005 032 755.9 filed Jul. 13, 2005, which is incorporated by reference herein in its entirety.

FIELD OF THE INVENTION

The present invention relates to a system for performing and monitoring minimally invasive interventions, particularly for the treatment of electrophysiological diseases.

BACKGROUND OF THE INVENTION

The serious cardiological diseases include the tachycardial arrhythmias, such as atrial fibrillation for example. In this situation, the vestibule is very frequently excited by conduction disturbances in the heart. In the case of other, for example ventricular, tachycardias the result is a complete contraction and thus an inadequate pumping performance by the heart. In the past, an attempt was made either to reduce the effect of the atrial fibrillation by means of a continuous intake of medicines or to eliminate the cause of the atrial fibrillation by means of a heart operation in which the conduction tissue is severed in certain parts of the vestibule. This surgical treatment does however have a relatively high risk for the patient. A minimally invasive therapy method has been establishing itself in recent times. In this situation, an ablation catheter is inserted into the vestibule with access through a vein. The ablation catheter then allows the disruptive conduction paths to be severed using electrical energy, high-frequency radiation for example. In this minimally invasive therapy, the disruptive conduction paths must be obvious to the doctor treating the condition in order that they can be correctly targeted by the ablation catheter. To this end, as a rule a mapping catheter is inserted with which the electrophysiological potentials in the heart are recorded with local resolution prior to the therapy and displayed on a monitor.

The minimally invasive diagnosis and therapy of tachycardial arrhythmias is carried out in an electrophysiological laboratory in which an angiographic X-ray unit, a device for recording an intracardiac ECG, a mapping catheter and also the ablation catheter are available. The method itself is generally referred to in electrophysiology as high-frequency ablation or RF ablation. The method for measuring the electrophysiological potentials in the heart in order to determine the ablation location in each case with the mapping catheter is referred to as mapping.

A method and a device for supporting the diagnosis and RF ablation and also the mapping are known from U.S. Pat. No. 6,556,695 B1, which provide the user with an enhanced navigation capability during the actual ablation procedure. With regard to the method, before the procedure commences 3D images of the heart are produced by means of a 3D imaging arrangement, in particular a computer tomograph or a magnetic resonance tomograph. These 3D images are registered using the coordinate system of the mapping catheters such that the 3D images can be displayed superimposed together with the mapping data. During the execution of the procedure, 2D images are additionally recorded using an intracardiac ultrasound catheter and are likewise superimposed on the displayed image data in order to provide the medical user with updated information for orientation and navigation purposes during the procedure. Use of this technique does however require that 3D images be recorded in a different station before the procedure since as a rule no computer tomograph or magnetic resonance tomograph is available in an electrophysiological laboratory. This means an increased time requirement for patient and hospital personnel.

SUMMARY OF THE INVENTION

The object of the present invention is to set down a system for performing and monitoring minimally invasive interventions, particularly for the treatment of electrophysiological diseases, which covers the workflow in its entirety from the examination through to the therapy, such that all the steps required for the treatment can be carried out in an electrophysiological laboratory.

The object is achieved by the system according to the independent Claim. Advantageous embodiments of the system are set down in the subclaims or emerge from the following description and also the embodiment.

The present system comprises an X-ray unit, in which at least one X-ray source and one X-ray detector can traverse a circular track through an angle range <360°, whereby the X-ray unit is preferably a C-arm X-ray unit for angiographic and/or cardiological imaging, an ECG recording unit, an imaging catheter, a mapping unit with a mapping catheter and an ablation unit with an ablation catheter. In addition, the system includes a control and evaluation unit which has interfaces at least for the X-ray unit, the ECG recording unit, the mapping unit, the ablation unit and the imaging catheter for exchanging data with these devices or catheters. The control and evaluation unit in the present system is designed for processing measurement and/or image data which it receives by way of the interfaces from the catheters and units, and for controlling the catheters and units for the capture of the measurement and/or image data. For this purpose the control and evaluation unit preferably has a data bus over which the interfaces can exchange data with one another and with modules of the control and evaluation unit. In addition, an operator interface for centralized operation of all the catheters and units and also a screen for the centralized display of the measurement and/or image data, and/or data derived from the latter, captured by the catheters and units are preferably provided.

The present system allows all the steps needed for treating tachycardial arrhythmias to be carried out in an electrophysiological laboratory without requiring further imaging resources. All tachycardial arrhythmias can thus be eliminated reliably, at little risk to the patient and to the clinical staff, with a high level of quality and with good therapeutic success. In this situation, the system is not dependent on preliminary images from computer tomographs or magnetic resonance tomographs. Rather, the present system allows 3D image data to be generated in real time and for example to have 2D images superimposed on it. With the existing system, the 3D images are captured by the X-ray unit configured for this purpose, which allows a 3D image data set to be reconstructed from different selectable projections. The techniques for the reconstruction of a 3D image data set from images taken by the X-ray unit employed in the present system, in particular a C-arm X-ray unit, are known as a general principle. 3D images of a skull and the vessels, for example, can thus be obtained by using the AXIOM Artis® FA/FB equipment from Siemens with an associated workstation. A method for generating a volume date set is likewise known from US 2004/0066906 A1. Further examples of C-arm X-ray units which deliver 3D images are described in Electromedica 70 (2002) No. 1, "Initial Clinical Experiences with the SIREMOBIL ISO-C$^{3D}$" by Euler et al. on pages 48 to 51, in DE 100 47 364 A1, in U.S. Pat. No. 6,379,041 or in DE 103 06 068 A1. The majority of previously known solutions however utilize a mobile C-arm X-ray unit for generating the 3D X-ray images. Such types of mobile devices do not however as a rule achieve levels of X-ray performance which are sufficient for cardiological images. A stationary X-ray unit, for example an AXIOM Artis® FC, TC or BC with a flat detector, is therefore to be preferred for the present system.

In this case the control and evaluation unit should have the corresponding module for the reconstruction of a 3D image data set from the image data obtained using X-ray unit of such a type. Furthermore, the control and evaluation unit should also have a correction module for correcting the image data, which enables the display of soft parts ("soft tissue"), particularly moving soft tissue. The correction to be performed in this situation can be chosen from the group comprising truncation correction, scatter correction, irradiation correction, ring artifact correction, correction of the beam hardening and of the low frequency drop. It is also possible to provide a separate correction processor in the control and evaluation unit for performing these corrections. An example of an X-ray unit with suitable correction modules in a workstation is the DynaCT® equipment from Siemens. In addition to the 3D images, 2D X-ray images (fluoroscopy) can naturally also be produced with the present X-ray unit.

A further significant advantage of the present system consists in the capability for data exchange between all the connected units. In this situation the operator does not need to transfer any data or information whatsoever from one unit to the other unit in question, or enter any data or information there. Rather, the central control and evaluation unit ensures at all times that all the connected units have at their disposal at all times the data required for their use from the other unit or units. In particular, the present system can be operated in the preferred embodiment by way of a central operator interface at which all the required information and data is available. In this embodiment, at least one central screen is also provided, on which all the data generated by the different units or catheters is displayed, superimposed if need be.

Even though the present system does not require any 3D image data recorded beforehand from a computer tomograph or a magnetic resonance tomograph in order to perform and monitor a minimally invasive procedure, then in one embodiment of the present system it is nevertheless possible to provide the capability to store 3D image data of this kind in the system and to use the system to display it, with other image or measurement data superimposed if need be. In this case an appropriate interface is provided for the feed of external 3D image data of this kind, for example in the form of a DICOM interface. Furthermore, the control and evaluation unit then comprises an appropriate module for registering 3D image data of this kind with the coordinate system of one or more units or catheters of the present system and also for the image display of the external 3D image data superimposed with image or measurement data from the catheters or units. In this situation the external 3D image data can also be updated with current image data from the X-ray unit or the imaging catheter.

Even though the present invention is described primarily with reference to the application for examination and therapy in the chambers of the heart, in particular for the treatment of tachycardial arrhythmias, it is evident that the system according to the invention can also be used for other vascular examinations and organ examinations, including their minimally invasive therapies.

BRIEF DESCRIPTION OF THE DRAWINGS

The present system is described in detail again in the following with reference to an embodiment in conjunction with the attached FIGURE which shows an illustration of the system in an embodiment which contains numerous optional components.

DETAILED DESCRIPTION OF THE INVENTION

The attached FIGURE shows an illustration of the system in an embodiment which contains numerous optional components. The area enclosed within the dashed line here denotes the control and evaluation unit 1 with the associated modules. It is naturally also possible however for individual ones of these modules to be designed as part of the individual units, particularly if these modules perform a preprocessing of the captured measurement or image data which is as a rule required in the case of units or catheters of this kind.

The system illustrated in the FIGURE by way of example comprises an X-ray unit for cardiological examination which has at least one C-arm with an X-ray source 2, a radiation shutter and also an X-ray detector 3, for example with a flat detector or aSi detector, and a patient positioning table 4. In this situation the patient positioning table 4 can have an X-ray transparent surface for patient positioning. In the preferred embodiment, this patient positioning table 4 enables longitudinal tilting and also lateral tilting with a swiveling capability of up to 90°, whereby all movements of the patient table can take place with motorized support. The X-ray source or sources 2 are connected to a high-voltage generator 5. Control of the X-ray images is effected by way of the system controller 6 which in the present example is implemented as a module in the control and evaluation unit 1. When a 3D imaging process is taking place, the C-arm travels through an angle range of at least 180° and takes projection images in rapid succession. The raw data recorded during this process is first preprocessed in a preprocessing module 7. The reconstruction of a 3D image takes place in the image processing module 8 for X-ray images. Both modules 7, 8 each form part of the control and evaluation unit 1 in the present example.

The 3D images captured can additionally be supported by the application of contrast agents. On account of the movement of the heart, ECG control is required in order to allow the 3D reconstruction from the 2D image data to be performed in the same heart phase in each case. The ECG unit required for this purpose is not shown explicitly in the FIGURE. The control and evaluation unit 1 does however have a corresponding connection 12 for physiological sensors, to which the ECG unit is connected. The ECG data is processed in the associated signal processing module 13 for physiological signal processing. This module 13 also processes other signals, such as an iECG signal and also other physiological signals, preferably relating to blood pressure, breathing and body temperature. The data captured, which is received by way of the connection 12, can be displayed or superimposed on a screen together with image information from other units. Methods for reconstructing the 3D images of a moving heart are known to the person skilled in the art from US 2002/0181645 A1 or 2005/0058248 A1, for example.

In addition to the latterly mentioned methods, the 3D images can also be generated from a small number of projections using discrete tomography techniques, particularly after a first 3D image data set has been generated at high resolution. One method for discrete tomography is described for example in US 2004/0008882 A1. An image capture technique of this type has the advantage that the patient and the clinical personnel are subjected to only slight radiation exposure as a result of the small number of projections required.

In the present example the control and evaluation unit 1 includes an image correction module 10, preferably with a separate processor unit, for the elimination of motion artifacts which are caused by breathing. In order to eliminate the breathing artifacts, at least one patient movement sensor 11 is provided which can for example be integrated into a breast-band for the patient. The one or more sensors 11 in this breast-band deliver data relating to breath amplitude and frequency which is utilized in the image correction module 10 for correction calculations that work out the motion artifacts from the image information delivered by the X-ray unit. In this situation, a calibration module 9 is preferably also provided which performs a calibration of the X-ray imaging system, for example a geometry calibration, equalization calibration, intensity calibration and/or gain calibration. As a general principle, such types of calibration and image correction techniques for X-ray units are known to the person skilled in the art. In addition to the data from the sensor 11, the amplitude and frequency of the breathing can also be calculated from the contour of the ECG signal and fed to the image correction module 10. The display of soft tissue structure in the 2D or 3D X-ray images is made possible by employing this type of image correction and, if necessary, calibration.

Furthermore, it is also possible to use an auxiliary position sensor (with an electromagnetic operating principle, for example) in order to capture movements of the patient on the patient table 4. In order to create as few cable connections as possible with the patient and to achieve largely unimpaired access to the patient, this auxiliary sensor preferably takes a wireless form, using a Bluetooth transmitter unit for example. Alternatively, it is also possible to use an optical camera to capture the position of the patient and to correct patient movements or shifts in position by computational methods of pattern recognition in the relevant image processing module. As an additional option, the patient can be scanned with a laser beam in order to determine and correct shifts in position.

The proposed system preferably also comprises a facility for ultrasound examination with at least one ultrasound catheter, for example a so-called AcuNav catheter. One or more connections 14 are provided for imaging catheters on the control and evaluation unit 1 which is connected to a corresponding interface 15. This interface 15 is designed in the present example for AcuNav catheters and IVUS catheters (IVUS=intravascular ultrasound), for IntraMR catheters (IntraMR=intracorporal or intravascular magnetic resonance) and also for position sensors. Accordingly, in the present example the control and evaluation unit 1 also has a preprocessing module 16 as well as an image processing module 17 for OCT, a preprocessing module 18 for AcuNav, a preprocessing module 20 for IVUS, an image processing module 19 for AcuNav and IVUS, a preprocessing module 21 and also an image processing module 22 for IntraMR, a preprocessing module 23 and also an image processing module 24 for the position sensors.

When the ultrasound catheter is used, it is also possible to employ an ultrasound contrast agent in order to enhance the ultrasound imaging, particularly the 3D imaging. The ultrasound catheter is in this situation preferably provided with an actuator which allows three-dimensional ultrasound imaging virtually in real time. In this situation the actuator rotates the ultrasound catheter or its recording head through a particular angle in order to record 2D sectional images which can be combined to produce a 3D image. Alternatively, instead of a two-dimensional array consisting of send and receive units the recording head of the catheter can also contain a three-dimensional array.

In addition, the ultrasound catheter can be provided with a lumen having a diameter of about 0.5 to 2 mm, by means of which an appropriate OCT catheter (OCT: optical coherence tomography) can be introduced into the vessels and the heart chambers in order to view the ablated tissue locations in close-up at high resolution. Suitable OCT catheters are known for example from WO 00/43730 A1 or WO 01/11409 A2. In this situation the OCT catheter can additionally be provided with magnets in order that it can be directed into the appropriate position by means of an external magnetic field. An example of this is known from DE 102 55 957 A1. As an alternative to the magnets, mechanical control devices which utilize tension and compression effects on the catheter can be used to enable rotation and bending of the catheter. In addition, the OCT catheter can be provided with position sensors which enable position finding of the catheter in the space by way of external position sensors and thus allow 3D OCT images to be generated. To this end, methods can be used which are known for reconstructing 3D ultrasound images from 2D ultrasound images.

It is also possible to additionally provide the ultrasound catheter with magnets in order to achieve enhanced control of it. An example of this is described in U.S. Pat. No. 6,772,001 B2. As an alternative to the magnets, mechanical control devices which utilize tension and compression effects on the catheter can also be used here to enable rotation and bending of the catheter. The ultrasound catheter too can additionally be provided with position sensors which enable position finding of the catheter in the space by way of external position sensors and allow 3D OCT images to be generated. Methods to this end are known for example from US 2003/0220561 A1 or from US 2003/0199748 A1.

In addition or as an alternative to the lumen already mentioned, the ultrasound catheter can be provided with a further lumen having a diameter of about 0.5 to 3 mm, by means of which an appropriate IVUS catheter (IVUS: intravascular ultrasound) can be introduced into the vessels and the heart chambers in order to view the ablated tissue locations in close-up at high resolution. An IVUS catheter is described for example in EP 0 885 594 B1. Here too, the IVUS catheter can additionally be provided with magnets in order that it can be directed into the appropriate position by means of an external magnetic field. As an alternative to the magnets, mechanical control devices which utilize tension and compression effects on the catheter can be used to enable rotation and bending of the catheter in the space. In addition, the IVUS catheter can be provided with position sensors which enable position finding of the catheter in the space by way of external position sensors and thus allow 3D IVUS images to be generated.

As an alternative to the intracorporal ultrasound catheter described earlier, it is also possible to use an intracorporal MR catheter or an intravascular MR catheter which delivers high-resolution images of the vessels, heart chambers and medical instruments. This catheter too can additionally be provided with magnets in order that the catheter can be directed into the appropriate position by means of an external magnetic field. As an alternative to the magnets, mechanical control devices which utilize tension and compression effects on the catheter can be used to enable rotation and bending of the catheter. This catheter too can additionally be provided with position sensors which enable position finding of the catheter in the space by way of external position sensors and allow 3D images to be generated. To this end, the aforementioned methods which are also employed in the case of 3D image generation can be used.

The present system also includes a device for measuring and recording the electrical activities in the heart, in particular an intracardial ECG (iECG), referred to in the following as mapping unit 25. An example of such a mapping unit 25 with a mapping catheter is set down in U.S. Pat. No. 6,738,673 B2. In this situation, mapping catheters can be used which are in direct contact with the epicard and/or mapping catheters which are not in direct contact with the endocard. The mapping catheter of the mapping unit 25 can additionally be provided with magnets, permanent or electromagnets, in order that it can be controlled by means of an external magnetic field. As an alternative to the magnets, mechanical control devices which utilize tension and compression effects on the catheter can be used to enable rotation and bending of the catheter. In addition, the mapping catheter can be provided with position sensors which enable position finding of the catheter in the space by way of external position sensors and thus allow 3D potential field images to be generated. To this end, known methods can be used, for example electroanatomical mapping as is realized in the CARTO® System from Biosense Webster. Furthermore, contactless mapping with the aid of a balloon catheter can be used in which the potential distribution on the endocard of the heart is calculated with the aid of mathematical models. A further option consists in the method for calculating positions of electrodes on catheters with the aid of impressed currents, as is realized in the LocaLisa® System from Medtronic and the Navex® System from Endocardial Solutions. A system for position finding by means of ultrasound sensors fitted on the catheter, as is realized in the RPM® System from Biosense Webster, can also be used in this situation.

The present system also includes an ablation unit 26 for ablation of the undesired conduction paths with the aid of an ablation catheter. A device of this kind is known for example from U.S. Pat. No. 5,409,000 A1. In this situation, the ablation catheter can additionally be provided with magnets (permanent or electromagnets). As an alternative to the magnets, mechanical control devices which utilize tension and compression effects on the catheter can be used to enable rotation and bending of the catheter. In addition, the ablation catheter can be provided with position sensors which enable position finding of the catheter in the space by way of external position sensors, and thus relative to the 3D potential fields which have been recorded with the mapping catheter of the mapping unit 25. Electrical and magnetic alternating fields, ultrasound, laser beam, heat or cold probes can be used for generating the ablation energy. It is also possible to sever the conductors by delivering clinical, pharmaceutical and/or biological active agents with suitable ablation catheters.

The present system preferably also includes a subsystem for position detection of one or more of the catheters and medical instruments used that are provided with corresponding position sensors. Reference has already been made to this capability in the description of the individual catheters. Different possibilities result for this position detection. One preferred option is electromagnetic position determination, for example using MPS (Magnetic Position System) from MediGuide, as is described in US 2002/0049375 A1. In addition to the solution described there, the invention proposes that the image information from MPS be combined with or superimposed on the medical images described above, preferably the 3D images. As is known, this requires calibration and registration of the different subsystems for the subsequent image fusion. For the calibration, the tip of the guide wire of the catheter is imaged at least once by at least two X-ray projections in the space (x, y, z) and the position in the space is determined at least once by the electromagnetic positioning system (x', y', z'). The two positions are then calibrated to one another with a transformation. It is advantageous in this situation if the calibration is performed only after the installation in the electrophysiological laboratory. The accuracy of the calibration can be increased through the use of a body phantom and a calibration involving multiple points.

The positions and images determined with the position sensor can be superimposed in 2D, 3D and 4D with images which have been generated using the following techniques: sonography, including IVUS and AcuNav methods, radiography, transillumination (fluoroscopy), angiography, optical coherence tomography (OCT), discrete tomography, positron emission tomography (PET), single photon emission computed tomography (SPECT), further diagnostic nuclear medicine, computer tomography, core spin tomography including catheter MR, optical images including endoscopy, fluorescence and optical markers (molecular imaging).

The coils required for the electromagnetic position determination in the position sensor on the catheter or medical instrument are preferably not arranged exclusively orthogonally with respect to one another but at an arbitrary angle of for example 60° in order to achieve better miniaturization. This miniaturization allows better integration of the position sensors in a catheter. The deviation from the orthogonal arrangement can be corrected by means of corresponding computing algorithms in the image processing module 24 for the position sensors. In order to improve the miniaturization, only one electrical conductor per sensor coil is fed back to the signal connections. The conducting guide wire of the catheter and also the human body with its blood vessels are used as the neutral electrode. In addition, a signal multiplexer which cyclically interrogates the receive antennas can be integrated into the tip of the guide wire. This results in a further reduction in the signal lines required. In addition, the send coils can also be operated and evaluated cyclically, at particular time intervals, at different frequencies, in order to increase the accuracy of the position finding. In this situation the electromagnetic position sensors can be designed such that, through the use of iron cores for example, when appropriately energized they can optionally also serve as electromagnets for controlling the respective catheter with an external magnetic field.

By preference, the subsystem for position detection also includes a calibration unit which stores the static and dynamic magnetic fields in the different function stages, resulting for example from movements of the C-arm of the X-ray unit, and takes this information into consideration during signal evaluation and correction calculation for image preparation. The individual components of the subsystem for position detection, particularly function units and signal lines, are equipped with devices which shield the physiological signals and image signals and also the signal processing and preparation from the magnetic fields of the send antennas. One of the solutions can be to coat the components with a conducting metal sheathing, of copper for example. Another possibility is coating with a thin-film layer consisting of conducting nanoparticles (for example nanoparticle silicon dioxide, aluminum oxide, silicon nitride, carbon). First attempts at magnetic shielding have been carried out by Biophan (cf. http://www.biophan.com/shielding.php). Magnetic shields using nanoparticles are known from U.S. Pat. No. 6,506,972 B1. The miniaturization of the position sensors can be additionally increased through the use of nanotechnology in their manufacture.

Other position determination techniques are naturally also possible in addition to electromagnetic position determination, thus for example using ultrasound, as is described for example in U.S. Pat. No. 6,038,468 A.

An appropriate subsystem can be provided for magnetic navigation of the catheters, which comprises corresponding magnets, mechanical fixtures, control electronics and operating units for the navigation system, whereby the operating units are in turn implemented in the control and evaluation unit 1. An example of such a subsystem is known from U.S. Pat. No. 6,148,823 A. Such a subsystem is however only available as an option for the present system, as is similarly a 3D color Doppler unit 27 which can deliver additional image information when required with an ultrasound probe mounted outside the thorax of the patient. These images can be superimposed with the other 2D, 3D and 4D images obtained by the X-ray unit or the catheters. The image fusion module 28 required for this is an important part of the present control and evaluation unit 1. This image fusion module 28 is used for the segmentation, auto-segmentation, registration, image reconstruction and image superimposition of the different measurement and image data received from the individual components of the present system. Suitable techniques for registration, image segmentation and image superimposition, particularly 2D-2D, 2D-3D, 3D-3D, 2D-4D and 3D-4D, are known to the person skilled in the art. Such forms of superimposition offer previously unavailable diagnostic benefits. Examples of such types of image fusions are known from DE 102 10 645 A1, DE 102 10 646 A1 or U.S. Pat. No. 5,706,416 A1.

In this situation, the present system also allows the intracardiac electrical activities recorded with the mapping catheter to be superimposed with the medical images, particularly the anatomical images of the heart. For the registration or superimposition of the image data from the patient with the position data from the catheters it is necessary to transfer the spatial coordinates of both objects into a common coordinate system. In this situation, the movements of the patient on the examination table can for example be determined by using the auxiliary position sensor already mentioned further above.

The control and evaluation unit 1 which constitutes the digital image system is preferably set up as an integrated computing unit with processor(s), memory (memories) and one or more screens, but can also be formed from a plurality of distributed computing units (workstations). An important feature consists however in the fact that the system can be operated with a central user interface 29 (user input/output unit) with an associated display unit 30. All inputs and control commands for the system can be entered by way of the user interface 29. The medical images generated, preferably AcuNav/OCT/IVUS/IntraMR/position sensor and X-ray images, are displayed—in an appropriately superimposed display where applicable—on the display unit which can also consist of a plurality of screens situated alongside one another. The CT or MR images which need to be produced prior to the procedure and which are optionally likewise stored in the system are also displayed on this display unit 30. By this means the information relating to the corresponding images is visible to the user at one place, thus enabling faster and better diagnosis.

The display unit 30 can include an appropriate 3D display for displaying 3D images, preferably in the form of a flat screen such as is known for example from Technology-Report CT IRC TIS from Siemens, "Autostereoskopische 3D-Displays and -verfahren" [autostereoscpic 3D displays and methods], October 2003, by Ulrich Walter and Dr. Eckart Hundt. This solution allows three-dimensional observation without supplementary devices such as 3D glasses for example. To this end, a suitable 3D display controller 31 is required. In addition, the observer can wear a headband or normal glasses with position sensors such that the viewing direction of the observer can be synchronized with the observation direction of the 3D object displayed on the screen by way of corresponding processors. An example for determining the viewing direction of an observer when tracking an image object can be found for example in U.S. Pat. No. 5,646,525 A. A corresponding receiver 32 for receiving data from which a head movement of the observer can be ascertained must be provided for this purpose on the 3D display controller 31.

With regard to the present system, the operating units for the X-ray unit, the AcuNav/OCT/IVUS units, the magnetic navigation system, the electrophysiological mapping units and also the ablation unit are combined or connected in an integrated solution according to the medical workflow. With the present system it is possible to dispense with the preliminary images from CT or MR. In addition to solutions already known, it is possible with the present system to generate 3D image data in real time and superimposed with 2D images. By employing an MPS subsystem it is possible to reduce the use of contrast agents and the X-ray dose applied. This embodiment also has the advantage that in addition to the angiographic X-ray method good images of the heart wall are obtained through the 3D ultrasound imaging and thus the state before and after an ablation can be displayed. The present system is not restricted to the treatment of tachycardial arrhythmias but can also be used as a variation for minimally invasive interventions of any type on the heart and in other organs, for heart valve repair for example.

The present system preferably contains a DICOM interface 33 for exchanging patient data and image data with a hospital information system (HIS) and also an interface 36 for receiving images produced by other arrangements (CT, MR, PET, SPECT for example). Furthermore, an image data memory 34 is provided for storing the processed image data. The corresponding power supply unit 35 for the system is also indicated in the FIGURE.

An essential feature of the present system consists in the fact that all measurement, image, control and, where applicable, patient data can be exchanged between the individual modules or components of the system by way of a common data bus 37. In this manner, the data provided by the different components and modules is available at any time at the other locations at which is it required.

The connections for the physiological sensors and the catheters are preferably decoupled from any mains voltage by way of an appropriate electrical isolation facility so as to not endanger the patient. Optical decoupling is particularly advantageous in this situation. In an advantageous embodiment of the system, all subsystems can be designed to be magnetically compatible such that they function normally in the environment of a magnetic navigation system.

The display of the 3D images by the display unit 30 preferably takes place using standard hardware from the PC/video/games industry, for example using 3D graphics cards or chips from ATI or Nividia. This offers a cost-effective solution for 3D display, volume rendering and shading.

As a supplement to the present system, the invention proposes that a temperature sensor which registers the temperature in the area of the ablation location be mounted on the tip of at least one of the catheters used for the procedure, preferably on the tip of the ablation catheter. Conclusions can then be drawn by way of this temperature concerning a successful ablation.

In addition, the invention proposes that a pressure sensor which registers the pressure in the heart chamber in the area of the ablation location be mounted on the tip of at least one catheter used for the procedure. By this means also it is possible to draw conclusions about the procedure, for example concerning a short-term pressure increase during the vaporization or ablation of tissue. A suitable miniature pressure sensor is known for example from U.S. 2003/0040674 A1, which is integrated in a guide wire. Alternatively, it is also possible to sense the normal blood pressure in the heart chambers such that the introduction of a separate blood pressure catheter can be avoided.

As a further supplement to the present system, the invention proposes a subsystem for applying an anesthetic, for example an anesthesia respirator 38, such as is commercially available. In addition, it is also possible to provide a defibrillator or heart pacemaker 39 for defibrillation and heart pacemaker stimulation for cardiological emergencies.

As an additional supplement, the system can also contain a hemodynamic measuring system which enables a standardized evaluation of the pressure and temperature measurements. Examples of this are the Sensis® and Cathcor® systems from Siemens.

Further additional subsystems which can be used as part of the present system are a patient monitoring system for monitoring the vital functions of a patient or a contrast agent injector to enable displays of cavity structures in the heart and vessels. With the patient monitoring system, it is for example possible to trigger an alarm if certain limits for the vital parameters of a patient are not reached or are exceeded.

Three sample courses of action when using the system described by way of example are demonstrated in the following. The following basic steps are performed in the first example:

Before the actual procedure:
recording of the demographic data for the patient in the hospital information system,
transfer of the patient information to a high-resolution 3D examination unit (CT, MR),
recording and reconstruction of the high-resolution 3D images or data sets,
preferably automatic segmentation of the relevant image area, and
transfer of the patient information and high-resolution 3D data sets to the present system.
During the procedure:
calibration of the ultrasound catheter with position sensors and registration with the available high-resolution 3D images,
introduction of the ultrasound catheter under X-ray control and/or with the aid of the position detection system,
updating (segmentation, registration, fusion) in the target area of the available high-resolution 3D image with current 3D ultrasound data,
introduction of the mapping catheter and recording of the intracardiac ECG under X-ray control and/or with the aid of the position detection system,
updating (segmentation, registration, fusion) in the target area of the available high-resolution 3D image with current 3D ultrasound data,
superimposition of the mapping images with the anatomical image of the heart chambers, introduction of the ablation catheter under X-ray control and/or with the aid of the position detection system,
updating (segmentation, registration, fusion) in the target area of the available high-resolution 3D image with current 3D ultrasound data,
ablation of the selected tissue locations,
checking the ablation by OCT catheter and/or temperature measurement and/or pressure measurement or renewed mapping or with other methods known to the person skilled in the art,
removal of all medical instruments and supplementary devices from the target area,
documentation and archiving of the procedure in the HIS,
discharge of the patient,
preparation of the accounting and billing by the HIS, for example with support by DICOM-MPPS (Modality Performed Procedure Step),
as an alternative to the ultrasound catheter the procedure can be performed with an MR catheter, and
as an alternative to the OCT catheter an IVUS catheter can be used.

The second example provides the following basic steps which are all performed during the procedure. No method steps are required before the actual procedure:
recording of the demographic data for the patient in the hospital information system,
recording and reconstruction of the high-resolution 3D images or data sets with the C-arm X-ray system (with the capability to display soft parts, known for example from Siemens as DynaCT®),
preferably automatic segmentation of the relevant image area,
calibration of the ultrasound catheter with position sensors and registration with the recorded high-resolution 3D images from the C-arm X-ray unit,
introduction of the ultrasound catheter under X-ray control and/or with the aid of the position detection system,
updating (segmentation, registration, fusion) in the target area of the available high-resolution 3D image with current 2D and/or 3D ultrasound data,
introduction of the mapping catheter and recording of the intracardiac ECG under X-ray control and/or with the aid of the position detection system,
updating (segmentation, registration, fusion) in the target area of the available high-resolution 3D image with current 2D and/or 3D ultrasound data,
superimposition of the mapping images with the anatomical image of the heart chambers,
introduction of the ablation catheter under X-ray control and/or with the aid of the position detection system,
updating (segmentation, registration, fusion) in the target area of the available high-resolution 3D image with current 2D and/or 3D ultrasound data,
ablation of the selected tissue locations,
checking the ablation by OCT catheter and/or temperature measurement and/or pressure measurement or renewed mapping or with other methods known to the person skilled in the art,
removal of all medical instruments and supplementary devices from the target area,
documentation and archiving of the procedure in the HIS,
discharge of the patient,
preparation of the accounting and billing by the HIS, for example with support by DICOM-MPPS,
as an alternative to the ultrasound catheter the procedure can be performed with an MR catheter,
as an alternative, during the procedure a new 3D X-ray image which is used for an update of the high-resolution 3D X-ray images can be produced from a small number of projections, and as an alternative to the OCT catheter an IVUS catheter can be used.

The following basic steps are performed in the third example:

Before the actual procedure:
As for the first example
During the procedure:
recording and reconstruction of the high-resolution 3D images or data sets with the C-arm X-ray unit and updating (segmentation, registration, fusion) of the high-resolution 3D images produced prior to the procedure (CT or MR) using the C-arm X-ray images (with the capability to display soft parts, known for example from Siemens as DynaCT®),
preferably automatic segmentation of the relevant image area,
calibration of the ultrasound catheter with position sensors and registration with the available high-resolution 3D images,
introduction of the ultrasound catheter under X-ray control and/or with the aid of the position detection system,
updating (segmentation, registration, fusion) in the target area of the available high-resolution 3D image with current 3D ultrasound data,
introduction of the mapping catheter and recording of the intracardiac ECG under X-ray control and/or with the aid of the position detection system,
updating (segmentation, registration, fusion) in the target area of the available high-resolution 3D image with current 3D ultrasound data,
superimposition of the mapping images with the anatomical image of the heart chambers, introduction of the ablation catheter under X-ray control and/or with the aid of the position detection system,
updating (segmentation, registration, fusion) in the target area of the available high-resolution 3D image with current 3D ultrasound data,
ablation of the selected tissue locations,
checking the ablation by means of an OCT catheter and/or temperature measurement and/or pressure measurement or renewed mapping or with other methods known to the person skilled in the art,
removal of all medical instruments and supplementary devices from the target area,
documentation and archiving of the procedure in the HIS,
discharge of the patient,
preparation of the accounting and billing by the HIS, for example with support by DICOM-MPPS,
as an alternative to the ultrasound catheter the procedure can be performed with an MR catheter,
as an alternative, during the procedure a new 3D X-ray image which is used for an update of the high-resolution 3D X-ray images can be produced from a small number of projections, and
as an alternative to the OCT catheter an IVUS catheter can be used.

As a result of the minimally invasive interventions performed today in cardiology, three types of advantageous embodiments of the proposed system can be presented, each of which results from combining a subset of the described subsystems. An advantageous embodiment for the electrophysiological laboratory can thus be configured as a combination of the following subsystems or functionalities:

For the treatment of heart arrhythmias: a combination comprising ablation unit, C-arm X-ray unit (with the capability to display soft parts, known for example from Siemens as DynaCT®), a module for 2D-3D or 3D-3D registration, a module for processing preoperatively recorded 3D image data, a CARTO® mapping system, a module for image integration of electroanatomical data with anatomical data from CT, MR, ultrasound or other anatomical imaging methods, an AcuNav or intracardiac ultrasound catheter with 3D ultrasound device, a 3D ultrasound device, a module for updating 3D images with 2D images, or 3D images with 3D images, and also a subsystem for magnetic navigation.

For interventional cardiology: a combination of an OCT catheter, an IVUS catheter, an MPS position sensing system, a Paieon® workstation for the 3D reconstruction and display of vessels and heart pacemaker electrodes, a Biplan X-ray unit (preferably C-arm based), a module for the tomographic reconstruction of 3D images from a small number of projections from the X-ray unit, a subsystem for magnetic navigation, a device for inserting stents, and also a contrast agent injector.

For pediatrics, whereby there is a particular interest in reducing radiation exposure and contrast agent quantity for the child patients: a combination of an AcuNav catheter, a 3D ultrasound catheter, an OCT catheter, a Biplan X-ray unit (preferably C-arm based), a module for 2D-3D registration, a subsystem for magnetic navigation, an MPS position sensing system, a module for processing preoperative MR data, and also devices for effecting repairs to heart valves or for example septal defects.

The invention claimed is:

1. A system for performing and monitoring an invasive procedure for medical treatment of a patient in a laboratory, comprising:
   an x-ray unit having an x-ray source and an x-ray detector which traverse a circular track through an angle range less than 360°, said source and detector positionable about the patient while the patient undergoes the invasive procedure to effect image generation with x-ray data for real time monitoring of the invasive procedure;
   a plurality of sources of real time data including an ECG recording unit, an imaging catheter and a mapping unit with a mapping catheter;
   an ablation unit with an ablation catheter; and
   a control and evaluation unit which has interfaces with the x-ray unit, the ECG unit, the image catheter, the mapping unit, and the ablation unit for controlling the catheters and units and to capture, exchange, process and use real time data while performing the invasive procedure in the laboratory, the system configured so that real time data provided from the x-ray unit, the recording unit and the imaging catheter is provided to the control and evaluation unit by way of a common data bus,
   wherein a 3D image is recorded prior to performing the minimally invasive intervention and is updated with a current 3D image data generated from the x-ray unit, the imaging catheter or the mapping catheter when performing the minimally invasive intervention.

2. The system as claimed in claim 1, wherein the x-ray unit is a C-arm or a Biplan x-ray system for displaying a soft tissue and for generating an angiographic or a cardiological image of the patient.

3. The system as claimed in claim 1,
   wherein the imaging catheter is an magnetic resonance or an ultrasound catheter,
   wherein the ultrasound catheter has a lumen for introducing an optical coherence tomography or an intravascular ultrasound catheter into a vessel and a heart chamber of the patient.

4. The system as claimed in claim 1, wherein the control and evaluation unit comprises:
- an operator interface for centralized operation of the catheters and units,
- a 3D display screen for a centralized display of the captured data or a derived data from the capture data,
- a plurality of modules for:
  - registering and superimposing on the screen the captured data or the derived data from the capture data with an image data from the x-ray unit or from an external imaging arrangement,
  - segmenting the captured data or the derived data,
  - controlling the x-ray unit to record a 3D image data set,
  - generating a new 3D image data set from different x-ray projections of the x-ray unit by discrete tomography,
  - processing and displaying the recorded or the new generated 3D image data set or the image data from the external imaging arrangement,
  - eliminating a motion artifact from the captured data or the derived data,
  - evaluating a pressure and a temperature measurements.

5. The system as claimed in claim 4, wherein the control and evaluation unit is connected via the common data bus with:
- a navigation device for magnetic navigating the catheters which are equipped with a magnet,
- a position determination device for determining a three-dimensional position of the catheters by an ultrasound or an electromagnetic method with a position sensor which is equipped with the catheters,
  - wherein the position sensor consists a plurality of coils or antennas arranged at an angle with respect to each other,
  - wherein the coils are simultaneously used as the magnet for the magnetic navigation of the catheters,
- a 3D color Doppler unit with an ultrasound probe for delivering additional imaging information of the patient,
- a monitoring device for monitoring a vital function of the patient, and
- a contrast agent injector for injecting the contrast agent to display a cavity structure in a heart and vessel of the patient.

6. The system as claimed in claim 1, wherein one or more of the catheters have a temperature sensor or a pressure sensor.

7. The system as claimed in claim 1, wherein the system includes an anesthesia device.

8. The system as claimed in claim 1, wherein the ablation unit conducts the ablation by delivering a chemical, pharmaceutical or biological active agent into the patient or operates with an energy selected from the group consisting of: an electrical high-frequency field, a cryo technology, a laser technology, a focused ultrasound, a heat technology with a heated catheter tip, and a microwave technology.

9. The system as claimed in claim 1, wherein the system is used for treating an electrophysiological disease of the patient.

10. The system as claimed in claim 9, wherein the system is used for treating a tachycardial arrhythmias of the patient.

11. The system as claimed in claim 1, wherein the 3D image which is recorded prior to performing the minimally invasive intervention is:
- a high-resolution 3D image recorded using a computer tomography or magnetic resonance system, or
- a low-resolution 3D image recorded using a positron emission tomography or single photon emission computed tomography system.

12. The system as claimed in claim 1, wherein a 4D image data is reconstructed by supplementing a 3D image data with a time characteristic.

13. An operating method for operating a system which performs and monitors a minimally invasive intervention of a medical procedure of a patient, comprising:
- recording demographic data for the patient in a hospital information system;
- transferring the demographic data of the patient to a high-resolution 3D examination unit;
- recording and reconstructing a high-resolution 3D image data set with the same high-resolution 3D examination unit;
- segmenting a target area from the high-resolution 3D image data set;
- transferring the demographic data of the patient and the high-resolution 3D image data set to the system;
- calibrating an image catheter with a position sensor and registering with the high-resolution 3D image data set;
- introducing the image catheter into the patient while monitoring the patient with an x-ray imaging device to generate current image data;
- updating the target area in the high-resolution 3D image data set with the current image data;
- introducing a mapping catheter into the patient and recording an intracardiac ECG while monitoring the catheter with the x-ray imaging device thereby providing catheter images;
- superimposing the mapping catheter images and an anatomical image of a heart chamber;
- inserting an ablation catheter while monitoring the patient with the x-ray imaging device in order to position the ablation catheter; and
- ablating a selected tissue.

14. The operating method as claimed in claim 13, wherein the ablation is checked by a method selected from the group consisting of: an optical coherence tomography catheter, an intravascular ultrasound catheter, a temperature measurement, a pressure measurement, and a renewed mapping image.

15. The operating method as claimed in claim 13, wherein the image catheter is an ultrasound or a magnetic resonance catheter.

16. The operating method as claimed in claim 13, wherein the high-resolution 3D examination unit is selected from the group consisting of: a computer tomography unit, a magnetic resonance unit, and a C-arm x-ray system.

17. The operating method as claimed in claim 13,
wherein the x-ray device is a C-arm x-ray system,
wherein the high-resolution 3D image data set is generated by a computer tomography unit or a magnetic resonance unit and is updated with 3D image data generated by the C-arm x-ray system prior to the procedure.

18. The operating method as claimed in claim 13, wherein 3D x-ray image data is generated by the x-ray device from different x-ray projections and is used for updating the high-resolution 3D image data set during the procedure.

* * * * *